United States Patent
Cabib et al.

[11] Patent Number: 5,856,871
[45] Date of Patent: Jan. 5, 1999

[54] FILM THICKNESS MAPPING USING INTERFEROMETRIC SPECTRAL IMAGING

[75] Inventors: Dario Cabib, Timrat; Robert A. Buckwald, Ramat Ishay; Michael E. Adel, Zichron Yakov, all of Israel

[73] Assignee: Applied Spectral Imaging Ltd., Migdal Haemek, Israel

[21] Appl. No.: 776,063

[22] PCT Filed: Jul. 12, 1995

[86] PCT No.: PCT/US95/08708
§ 371 Date: Jan. 21, 1997
§ 102(e) Date: Jan. 21, 1997

[87] PCT Pub. No.: WO96/03615
PCT Pub. Date: Feb. 8, 1996

Related U.S. Application Data

[63] Continuation-in-part of Ser. No. 635,820, Apr. 22, 1996, which is a continuation-in-part of Ser. No. 575,191, Dec. 20, 1995, which is a continuation-in-part of Ser. No. 571,047, Dec. 12, 1995, which is a continuation-in-part of Ser. No. 392,019, Feb. 21, 1995, Pat. No. 5,539,517, which is a continuation-in-part of Ser. No. 107,673, Aug. 18, 1993, abandoned.

[30] Foreign Application Priority Data

Jul. 26, 1994 [IL] Israel ......................................... 110466

[51] Int. Cl.$^6$ ...................................................... G01B 9/02
[52] U.S. Cl. ............................. 356/346; 356/359; 356/357
[58] Field of Search ..................................... 356/345, 346, 356/352, 359, 360, 357

[56] References Cited

U.S. PATENT DOCUMENTS 5,341,205  8/1994  McLandrich et al. ................... 356/357

*Primary Examiner*—Robert Kim
*Attorney, Agent, or Firm*—Mark M. Friedman

[57] ABSTRACT

A method of determining the thickness map of a film (14) overlying a substrate (14). This method includes illuminating (10) the film simultaneously from different angles and analyzing spectral intensity of the radiation reflected by each point on the film (14). The analysis is effected by collecting reflected radiation from the film (14), passing the radiation through an interferometer (16) which outputs modulated radiation corresponding to a predetermined set of linear combinations of the spectral intensity of the radiation emitted from each pixel, simultaneously and separately scanning optical path differences generated in the interferometer (16) for each pixel, focusing the radiation outputted from the interferometer (16) on a detector array, and processing the output of the detector array to determine the spectral intensity of each pixel thereof to obtain a spectral intensity distribution. Finally, the method includes further processing the spectral intensity distribution to determine the spatial distribution of the thickness of the film (16).

16 Claims, 2 Drawing Sheets

FILM THICKNESS MAPPING USING INTERFEROMETRIC SPECTRAL IMAGING

This is a continuation in part of U.S. patent application Ser. No. 08/635,820, filed Apr. 22, 1996, which is a continuation in part of U.S. patent application Ser. No. 08/575, 191, filed Dec. 20, 1995, which is a continuation in part of U.S. patent application Ser. No. 08/571,047, filed Dec. 12, 1995, which is a continuation in part of U.S. patent application Ser. No. 08/392,019, filed Feb. 21, 1995, now U.S. Pat. No. 5,539,517, which is a continuation in part of U.S. patent application Ser. No. 08/107,673, filed Aug. 18, 1993, now abandoned.

FIELD AND BACKGROUND OF THE INVENTION

The present invention relates to a method and apparatus for spectral analysis of images to determine the thickness of a thin film, and particularly for spatially resolving film thicknesses of a coating deposited over the surface of a silicon wafer or other similar materials (for example, a flat panel display).

Measuring film thickness by reflectance spectroscopy is well known: see for example P. S. Hauge, "Polycrystalline silicon film thickness measurement from analysis of visible reflectance spectra", J. Opt. Soc. Am., No. 8, August 1979, and the book by Milton Ohring: "The material science of thin films", Academic Press Ltd., 1992. In today's microelectronic device manufacturing processes, the uniformity of the deposited films over a wafer is gaining importance as time goes on, because a good uniformity insures identity among the finished product chips. The size of the chips is also decreasing, so that the uniformity tolerance is becoming stricter. In addition, to insure high yield (low rejects) and efficient (low cost) manufacturing, the wafer inspection requires higher automation, shorter time, higher accuracy, and wider thickness range.

As a result, the film thickness map of the wafer, as one of the many inspections done during the manufacturing, must be done accurately, fast, on a large number of points (test sites), and at a wide thickness range.

Today, film thickness mapping instruments are based on ellipsometry or on reflectance spectroscopy. Only the latter is addressed herein. As examples of prior art in this field we mention the SpectraMap SM-300 and the FT-500 of Prometrix. The spectra are measured point by point by moving the wafer on a translation stage, in order to complete one thickness map. This takes time, it requires high movement accuracy, because of the high spatial resolution required, and increases the wafer handling, which is practical only when the wafer is outside a deposition chamber (therefore it cannot be done in-situ). In fact, the fastest thickness mapping mentioned by present manufacturers of film thickness equipment is hundreds of points in a few seconds.

There is thus a recognized need for, and it would be highly advantageous to have a method and apparatus for determining the spatial distribution of the thickness of a film overlying a substrate, more quickly, with higher spatial resolution (more test sites), without the need to move the wafer with respect to the measuring instrument when going from a test site to another (higher accuracy, and less wafer handling with the potential for in-situ monitoring), and easily measure the widest thickness range possible.

The present invention relates to a method and apparatus for mapping film thickness on Silicon wafers or similar substrates, which does not require moving the wafer (making the results faster and spatially more accurate, and potentially capable of being done in-situ), reaching tens of thousands of pixels in a few seconds (not hundreds as stated in the present commercial literature), and which has the potential to measure, in the same time as other potentially competing methods (mentioned below), a wider thickness range.

A spectrometer is an apparatus designed to accept light, to separate (disperse) it into its component wavelengths, and detect the spectrum. An imaging spectrometer is one which collects incident light from a scene and analyzes it to determine the spectral intensity of each pixel thereof.

The former measures the spectrum only at one point, therefore, with such an instrument, the wafer must be moved point by point relative to the instrument, and will have the above mentioned drawbacks of long measurement time and position accuracy.

The latter, i.e., an imaging spectrometer or spectral imager, can be of different types: a technology similar to the one used for resource mapping of the earth surface from airplanes and satellites could be used for film thickness mapping (see, for example, J. B. Wellman, Imaging Spectrometers for Terrestrial and Planetary Remote Sensing, SPIE Proceedings, Vol.: 750, p. 140 (1987)). However, this technique is based on grating technology to spectrally disperse the light: this brings the following drawback.

A grating has higher order diffraction: in order for it to be useful for spectral measurements, its spectral range must be limited by blocking the wavelengths outside a so called "octave" of wavelengths, for example 0.4 to $0.8\mu$; therefore an instrument based on a grating cannot have a wavelength range wider than one in which the ratio between the higher and the lower wavelength is larger than 2. This problem can be solved by measuring separately different octaves by rotating the grating to different angles, or by using several gratings simultaneously. However, these solutions increase the measurement time or complicate the instrument optics. The same problem is encountered by liquid crystal and acousto-optic crystal tunable filters. The importance of the wavelength range is related to the film thickness range to be measured by the instrument. In fact, as is well known in the optics literature, high precision film thickness measurements are difficult to obtain by reflection spectroscopy when the thickness t of the film is less than $(\lambda/4)n$, where $\lambda$ is the minimum wavelength of the instrument sensitivity range, and n is the refractive index of the film. Therefore, the wider the wavelength range to which the instrument is sensitive, the wider the thickness range that it can measure.

It is also well known (see, for example, the book R. J. Bell, "Introductory Fourier Transform Spectroscopy", Academic Press 1972), that interferometers do not have this limitation, and therefore can more easily measure a wider range of thicknesses.

Our U.S. Pat. No. 5,539,571, which is incorporated by reference in its entirety for all purposes as if fully set forth herein, discloses a method of analyzing an optical image of a scene to determine the spectral intensity of each pixel of the scene, which includes collecting incident light from the scene, passing the light through an interferometer which outputs modulated light corresponding to a predetermined set of linear combinations of the spectral intensity of the light emitted from each pixel; scanning the light beam entering the interferometer with respect to the interferometer or scanning the interferometer itself, to scan the optical path difference (OPD) generated in it for all the pixels of the scene separately and simultaneously; focusing the light outputted from the interferometer on a detector array, and processing the output of the detector array to determine the spectral intensity of each pixel thereof.

The above-referenced patent application provides a method and apparatus for spectral analysis of images which better utilizes all the information available from the collected incident light of the image to substantially decrease the film thickness measurement time, reach higher spatial resolution, and increase thickness dynamic range, as compared to other existing instrumentation. From here we can see how our method can give a thickness map of tens of thousands of pixels in a few seconds. Presently available detector matrices have 16,384 (128×128) pixels which are scanned at 1,000 frames per second (16 MHz). As a consequence, since each frame gives the separate and simultaneous information about the OPD of every pixel of the image (which is equivalent to the spectral information by Fourier Transform), at the end of a second all the needed spectral information is collected for all those pixels.

SUMMARY OF THE INVENTION

According to the present invention there is provided a method of determining the thickness map of a film overlying a substrate, comprising the steps of: (a) illuminating the film simultaneously from different angles; (b) analyzing spectral intensity of the radiation reflected by each point on the film, the analysis effected by: (A) collecting reflected radiation from the film; (B) passing the radiation through an interferometer which outputs modulated radiation corresponding to a predetermined set of linear combinations of the spectral intensity of the radiation emitted from each pixel; (C) simultaneously and separately scanning optical path differences generated in the interferometer for the each pixel; (D) focusing the radiation outputted from the interferometer on a detector array; and (E) processing the output of the detector array to determine the spectral intensity of each pixel thereof to obtain a spectral intensity distribution; and (c) further processing the spectral intensity distribution to determine the spatial distribution of the thickness of the film.

Also according to the present invention, there is provided an apparatus for determining the thickness map of a film overlying a substrate, comprising: (a) means for illuminating the film simultaneously from different angles; (b) means for collecting reflected radiation from the film; (c) an interferometer; (d) means for passing the radiation through the interferometer such that it outputs modulated radiation corresponding to a predetermined set of linear combinations of the spectral intensity of the radiation emitted from each pixel; (e) a detector array; (f) means for simultaneously and separately scanning optical path differences generated in the interferometer for each pixel; (g) means for focusing the radiation outputted from the interferometer on the detector array; (h) means for processing the output of the detector array to determine the spectral intensity of each pixel thereof to obtain a spectral intensity distribution; and (i) means for further processing the spectral intensity distribution to determine the spatial distribution of the thickness of the film for all the above pixels more quickly without wafer movement and with wider thickness range than other possible methods.

According to further features in preferred embodiments of the invention described below, the further processing includes use of constant angle reflection interference spectroscopy techniques (CARIS, see Ohring reference above), or other spectral analysis algorithms.

According to still further features in the described preferred embodiments, the further processing includes compensation for different angles of incidence of the radiation.

The present invention successfully addresses the shortcomings of the presently known configurations by providing a method and apparatus for film thickness mapping which is faster and more accurate, which does note require wafer movement and which is effective over a larger thickness range.

BRIEF DESCRIPTION OF THE DRAWINGS

The invention is herein described, by way of example only, with reference to the accompanying drawings, wherein.

DESCRIPTION OF THE PREFERRED EMBODIMENTS

The present invention is of an apparatus and method for measuring the spatial distribution of film thickness on a wafer or other optical material substrate, using spectral imaging.

The principles and operation of an apparatus and method according to the present invention may be better understood with reference to the drawings and the accompanying description.

Figure 1:
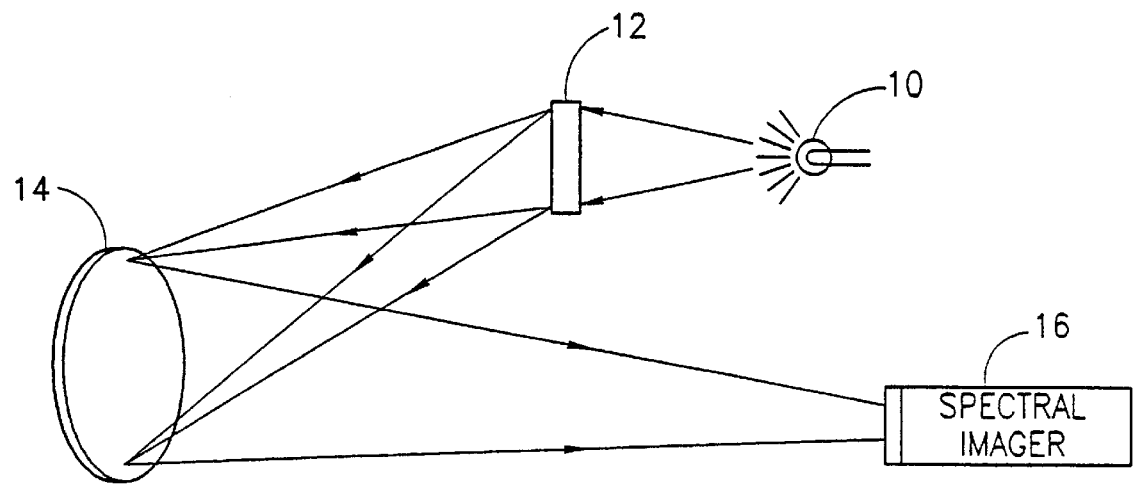
FIG. 1 schematically depicts an apparatus and method according to the present invention where the spectral imager is any of the various types described in U.S. Pat. No. 5,539,517.

Referring now to the drawings, FIG. 1 schematically depicts an apparatus and system according to the present invention. A suitable radiation source 10, preferably a light source, such as a halogen lamp, is passed through a diffuser 12. The light may be guided from source 10 to diffuser 12 through an optical fiber (not shown).

Light passing through diffuser 12 impinges on a wafer 14 on which is found the film whose film thickness distribution is to be determined. The angle of incidence of light from diffuser 12 onto wafer 14 relative to the normal varies. Preferably, the variation of incidence angle is accounted for in the processing of the data to determine the spatial thickness distribution of the film.

Some of the light emerging from the film on wafer 14 enters a spectral imaging system 16 which analyzes the optical image of the film to determine the spectral intensity of each pixel thereof and produce a spectral intensity distribution.

Spectral imaging system 16 is preferably of the type disclosed in U.S. Pat. No. 5,539,517 which is incorporated by reference in its entirety as if fully set herein. Briefly, spectral imaging system includes means for collecting incident radiation from the film, an interferometer, which is preferably a Sagnac, a Fabry-Perot or a Michelson interferometer, means for passing the light through the interferometer such that it outputs modulated light corresponding to a predetermined set of linear combinations of the spectral intensity of the light emitted from each pixel, scanning the light beam entering the interferometer with respect to the interferometer or scanning the interferometer itself, to scan the optical path difference (OPD) generated in it for all the pixels of the scene separately and simultaneously, a detector array, means for focusing the light outputted from the interferometer on the detector array, and means for processing the output of the detector array to determine the spectral intensity of each pixel thereof to obtain the spectral intensity distribution.

Figure 3:
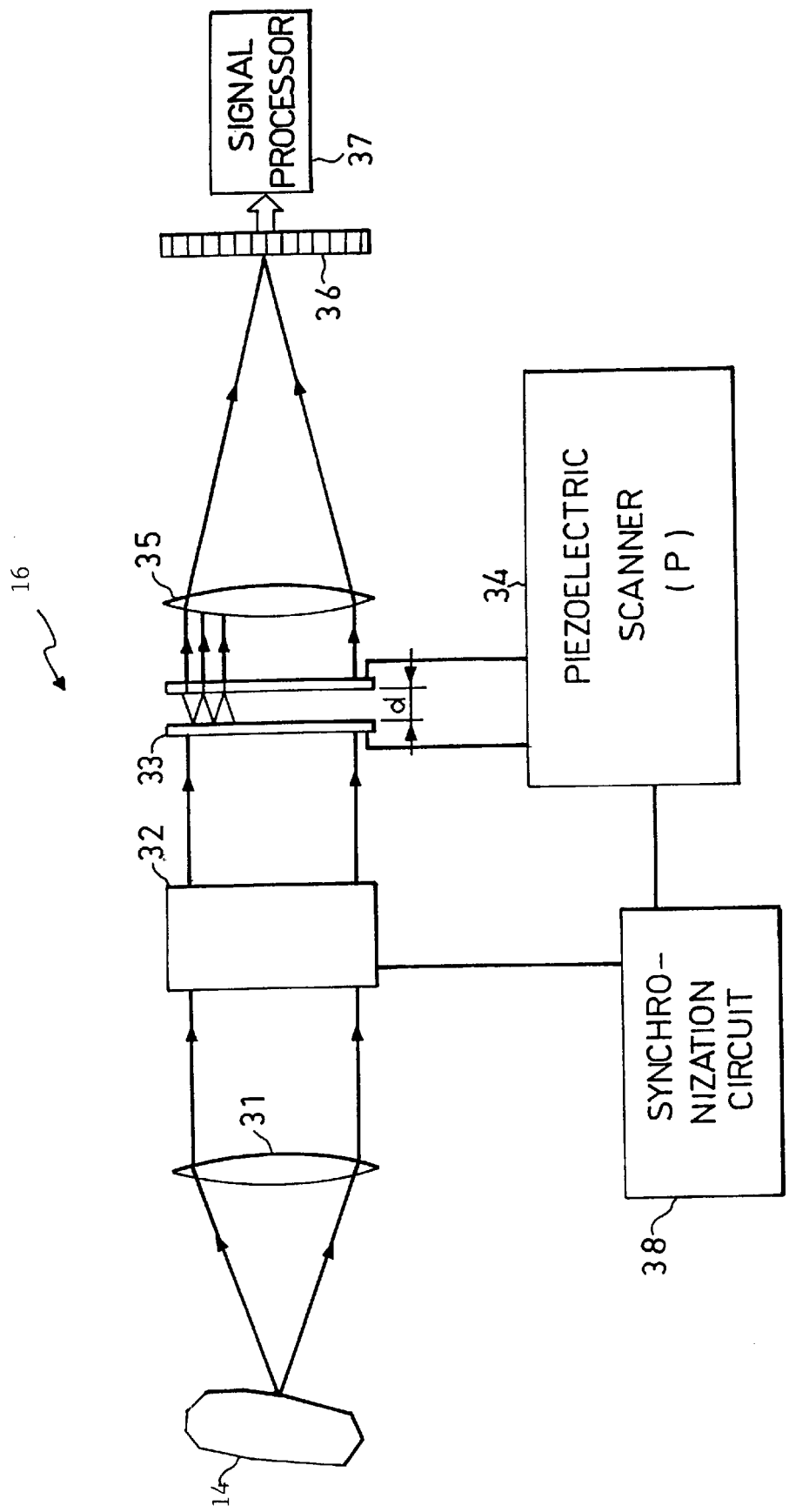
FIG. 3 is a diagram illustrating a spectral imager.

FIG. 3 illustrates one form of spectral imager 16, as described in U.S. patent application Ser. No. 08/107,673. Spectral imager 16 includes a collection optical system 31 that collects light from wafer 14 and directs the collected light as a substantially parallel beam to a one-dimensional mechanical scanner, e.g., a mirror scanner as indicated at 32, to scan wafer 14. The output from scanner 14 is fed to a Fabry-Perot interferometer 33 having an etalon made of two plane parallel reflectors spaced at a distance "d" from each other. The spacing distance "d" is varied by using a piezo-electric scanner 34. The output from Fabry-Perot interferomneter 33 is fed through a refocusing optical system 35 onto a one-dimensional array of detectors 36 whose outputs are fed to a signal processor 37. If a two-dimensional detector array is used, scanner 32 can be eliminated.

The spectral intensity distribution produced by spectral imaging system 16 is further processed, using, for example, a suitable computer 17, to determine the spatial distribution of the thickness of the film.

An apparatus and method according to the present invention may be used to carry out spectral imaging on silicon wafers in order to obtain spatially resolved film thickness over the wafer surface.

To use an apparatus and method according to the present invention one may start with a bare silicon wafer, i.e., a silicon wafer which does not bear a film on its surface. The bare wafer is placed on a suitable wafer positioned and the light source is aligned to give the best possible uniformity over the wafer area.

A spectral measurement taken from a single point or from all points on the wafer can serve as a "white calibration" to account for the spectral response of the system as a whole or a point by point basis. Following the calibration the bare wafer is replaced with the actual wafer the thickness of whose film is to be measured.

Various processing techniques can be utilized to convert the spectral data obtained into meaningful thickness information. One of the simplest is the technique of constant angle reflection interference spectroscopy (CARIS) (see, for example, M. Ohring, "The Material Science of Thin Films" Academic Press, 1991, ch. 6.2). In order to use this technique the thickness of the film must be such that at least two interference minima are observed within the spectral range of the instrument. In cases where more than two minima are observed in the measured spectral range the average d can be taken and a different n is then entered for each pair of minima. Other algorithms may be suitable in cases where there are no minima.

The accuracy and precision of an apparatus and method according to the present invention may be enhanced by increasing the uniformity of the illumination of the wafer. The performance could be further enhanced by taking into account the spatial variation in the angle of incidence of the incident radiation. Similarly, in assessing the spectral locations of the interference minima, it would be better to use a more sophisticated parabolic fit rather than using a fitted minimum.

Better computational techniques than the constant angle reflection interference spectroscopy techniques described above may be used to further enhance the performance of an apparatus and method according to the present invention. Thus, unlike the technique described herein for calculating film thickness which relies on spectra obtained by Fourier transformation of the point by point interferograms, more accurate results may be obtainable which allow for the direct calculation of film thickness from the interferograms rather than from the spectra. Such techniques may be particularly useful for film thickness calculations in cases of more than a single layer.

Figure 2:
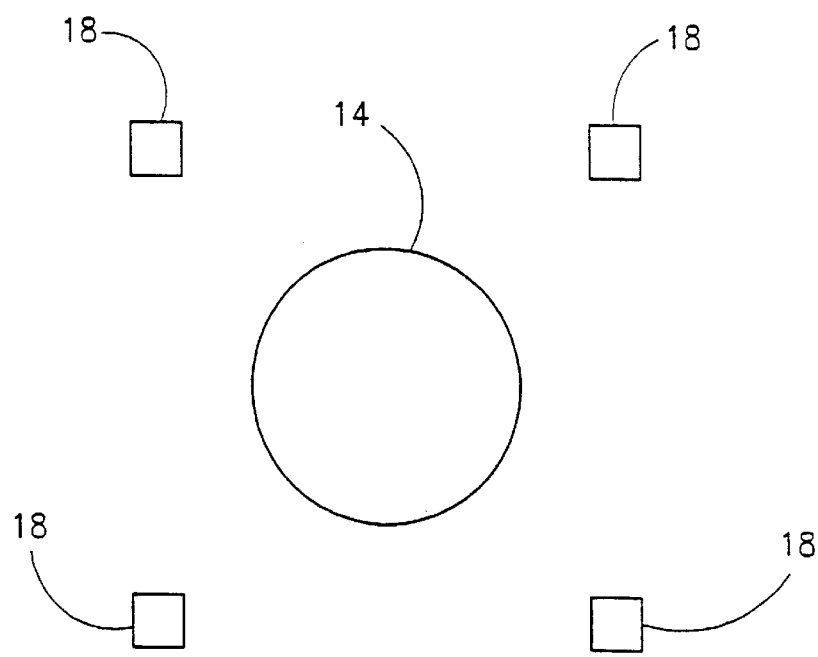
FIG. 2 shows a wafer surrounded by four reflectance standards for supplying real time compensation for illumination intensity drift.

Furthermore, apparatus and methods according to the present invention could be further improved by providing reflectance standards 18 (FIG. 2), preferably four, for supplying real time compensation for illumination intensity drift. These standards are preferably placed at the four corners of the spectral imager field of view and may be small pieces of silicon wafers. The spectral images of reflectance standards 18 are detected simultaneously with that of the wafer which allows for the real time compensation of time variations in any system parameters, such as light source, optics, electronics, and the like, thereby improving the measurement accuracy and repeatability.

Finally, an algorithm based on the spectral difference, pixel by pixel, and wavelength by wavelength between two spectral images, can be useful for inspection of semiconductor devices. For alignment of coatings, imperfections or deviations, contaminations, or other defects, the difference of two spectral images can be used to compare a device in production with a reference device, taken as standard.

While the invention has been described with respect to a limited number of embodiments, it will be appreciated that many variations, modifications and other applications of the invention may be made.

What is claimed is:

1. A method of determining the thickness map of a film overlying a substrate, comprising the steps of:
   (a) illuminating the film simultaneously from different angles;
   (b) analyzing spectral intensity of the radiation reflected by each point on the film, said analysis effected by:
      (A) collecting reflected radiation from the film;
      (B) passing the radiation through an interferometer which outputs modulated radiation corresponding to a predetermined set of linear combinations of the spectral intensity of the radiation emitted from each pixel;
      (C) simultaneously and separately scanning optical path differences generated in the interferometer for said each pixel;
      (D) focusing the radiation outputted from said interferometer on a detector array; and
      (E) processing the output of the detector array to determine the spectral intensity of each pixel thereof to obtain a spectral intensity distribution; and
   (c) further processing said spectral intensity distribution to determine the spatial distribution of the thickness of the film.

2. The method according to claim 1, wherein said interferometer is selected from the group consisting of Sagnac, Fabry-Perot and Michelson interferometer.

3. The method according to claim 1, wherein the different incident angles are achieved by directing said illumination of the film through a diffuser.

4. The method according to claim 1, further comprising diffusing said illuminating radiation prior to its incidence upon the film.

5. The method according to claim 1, further comprising obtaining an additional spectral image by measuring a reference wafer and wherein said further processing includes a point by point normalization based on said additional spectral image to compensate for variations in instrument response within its field of view and of illumination of different regions of the film.

6. The method according to claim 1, wherein said further processing includes compensation for different angles of incidence of said radiation.

7. An apparatus for determining the thickness map of a film overlying a substrate, comprising:
   (a) means for illuminating the film simultaneously from different angles;
   (b) means for collecting reflected radiation from the film;
   (c) an interferometer;
   (d) means for passing the radiation through said interferometer such that it outputs modulated radiation corresponding to a predetermined set of linear combinations of the spectral intensity of the radiation emitted from each pixel;
   (e) a detector array;
   (f) means for simultaneously and separately scanning optical path differences generated in the interferometer for said each pixel;
   (g) means for focusing the radiation outputted from said interferometer on said detector array;
   (h) means for processing the output of the detector array to determine the spectral intensity of each pixel thereof to obtain a spectral intensity distribution; and
   (i) means for further processing said spectral intensity distribution to determine the spatial distribution of the thickness of the film.

8. The apparatus according to claim 7, wherein said different angles are caused by a diffuser located in the path of the illuminating radiation.

9. The apparatus according to claim 7, wherein said interferometer is selected from the group consisting of Sagnac, Fabry-Perot and Michelson interferometer.

10. The apparatus according to claim 7, wherein said means for further processing includes means for performing a constant angle reflection interference spectroscopy technique.

11. The apparatus according to claim 7, wherein said means for further processing includes means for compensating for different angles of incidence of said radiation.

12. The apparatus according to claim 7, further comprising a plurality of reflectance standards for supplying real time compensation for illumination intensity, detector response and electronic drift.

13. The method according to claim 1, wherein said interferometer is of the moving type.

14. The method according to claim 1, wherein said detector array is two dimensional.

15. The apparatus according to claim 7, wherein said interferometer is of the moving type.

16. The apparatus according to claim 7, wherein said detector array is two dimensional.

* * * * *